United States Patent [19]

Bolduc

[11] 4,207,891

[45] Jun. 17, 1980

[54] DISPENSING INSTRUMENT WITH SUPPORTED BALLOON

[75] Inventor: Lee R. Bolduc, St. Petersburg, Fla.

[73] Assignee: Population Research Incorporated, Clearwater, Fla.

[21] Appl. No.: 950,170

[22] Filed: Oct. 10, 1978

[51] Int. Cl.² ............................................. A61M 1/00
[52] U.S. Cl. .................................... 128/235; 128/1 R
[58] Field of Search .................... 128/235, 349 B, 232, 128/216, 1 R, 260, 129, 130

[56] References Cited

U.S. PATENT DOCUMENTS

| | | | |
|---|---|---|---|
| 3,822,702 | 7/1974 | Bolduc et al. | 128/235 |
| 3,871,374 | 3/1975 | Bolduc et al. | 128/235 |
| 3,875,939 | 4/1975 | Bolduc et al. | 128/235 |
| 3,948,259 | 4/1976 | Bolduc et al. | 128/235 |
| 3,972,331 | 8/1976 | Bolduc et al. | 128/232 |
| 4,109,654 | 8/1978 | Bolduc et al. | 128/235 |
| 4,119,098 | 10/1978 | Bolduc et al. | 128/235 |

FOREIGN PATENT DOCUMENTS

| | | |
|---|---|---|
| 31-9697 | 6/1956 | Japan . |
| 35-9793 | 5/1960 | Japan . |
| 43-11090 | 5/1968 | Japan . |
| 43-31107 | 12/1968 | Japan . |

*Primary Examiner*—John D. Yasko
*Attorney, Agent, or Firm*—Burd, Bartz & Gutenkauf

[57] ABSTRACT

A fluid dispensing instrument having a dispenser operable to place a drug material into the uterine cavity of a female and an expandable balloon cooperating with balloon support structure operable to move the drug material from the uterine cavity into both canals of the Fallopian tubes of a female. The instrument has a housing carrying a piston and cylinder assembly. The balloon is attached to an elongated flexible tubular probe mounted on one end of the housing. The piston and cylinder assembly is operable to fully collapse the balloon prior to insertion through the cervical opening into the uterine cavity. After the balloon is inserted into the uterine cavity, an ampulla storing the drug material is loaded into the instrument. The piston and cylinder assembly is actuated to initially expand the balloon and move a plunger into the ampulla to dispense the drug material into the uterine cavity. The balloon is then fully expanded to move the drug material from the uterine cavity into the canals of the Fallopian tubes. The support structure cooperating with the balloon prevents the balloon from expanding back through the cervical opening into the vaginal passage. The support structure is a monofilament nylon arranged in intersecting latitudinal and longitudinal directions about a lower portion of the balloon.

28 Claims, 11 Drawing Figures

DISPENSING INSTRUMENT WITH SUPPORTED BALLOON

SUMMARY OF THE INVENTION

The invention is directed to a dispensing instrument for placing fluid and fluid like materials, as a drug material, into both canals of the Fallopian tubes of a primate female. The instrument is equipped with an expandable balloon that cooperates with support means which limit the enlargement of a portion of the balloon to prevent the balloon from expanding back through the cervical opening and into the vaginal passage. The balloon is mounted on the remote end of an elongated flexible probe attached to housing means of the instrument. Dispensing structure, including a piston and cylinder assembly, located within the housing is used to partially expand the balloon, dispense and drug material into the uterine cavity, and then fully expand the balloon to move the drug material from the uterine cavity into the canals of the Fallopian tubes. In one embodiment, the balloon support structure is latitudinally and longitudinally arranged intersecting filaments, as a monofilament nylon mesh, attached to the outside of the balloon with attaching means. The filaments are thin flexible members that do not interfere with the collapsing of the balloon about the probe, nor the enlargement of the section of the balloon cooperating with the support structure to a predetermined size. The supporting structure fortifies and reinforces the sheet member of the balloon so that portions of the sheet member do not expand through the cervical opening and enlarge in the vaginal passage.

In the utilization of the dispensing instrument, it has been found that the cervices of primate females have different sizes and lengths. Also, the uterine cavities have different shapes and elongated sections leading to the canals of the Fallopian tubes. In a number of patients with weak cervical muscles, non-supported balloons can expand back through the cervical openings into the uterine cavity. This impairs the pumping effectiveness of the portion of the balloon that expands in the uterine cavity. The supported balloon structure of the invention has overcome this disadvantage of the prior balloon structures.

Under certain circumstances, it is difficult to insert the balloon through the cervical opening into the uterine cavity. The relatively tight or strong cervix causes the air in the balloon to expand the balloon sheet material thereby increasing the difficulty of inserting the balloon through the cervical opening into the uterine cavity. The dispensing structure of the invention collapses the sheet member of the balloon tight against the probe. The support structure cooperating with the sheet member does not interfere with the collapsing of the sheet member on the probe so that it can be readily inserted through the cervical opening into the uterine cavity.

IN THE DRAWINGS

DESCRIPTION OF PREFERRED EMBODIMENT

Figure 1:
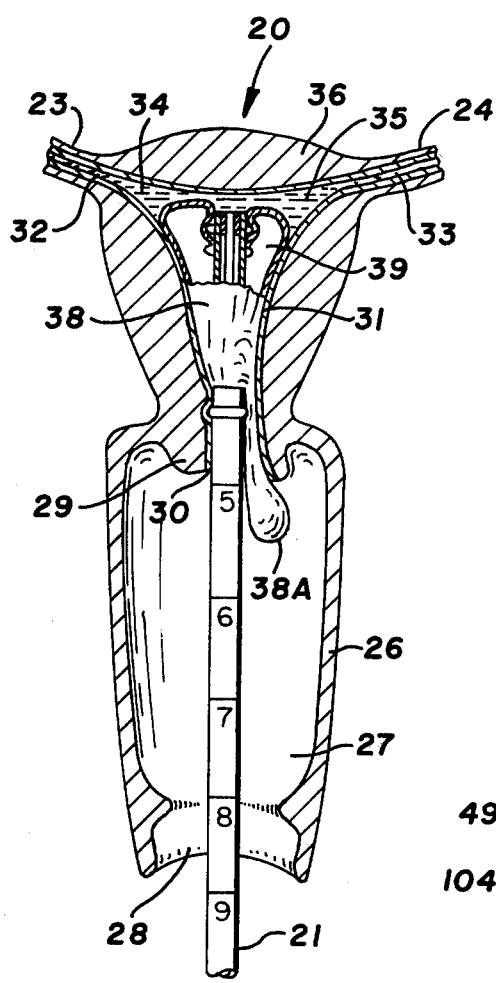
FIG. 1 is a sectional view of a female reproductive system with an inflated balloon on the end of a probe located in the uterine cavity.

Referring to FIG. 1, there is shown a female reproductive system indicated generaly at 20 of a primate female. A dispensing instrument is used to discharge a liquid type material into the uterine cavity and move the material into the canals of the Fallopian tubes. The instrument (not shown) can be the structure shown in U.S. Pat. No. 3,871,374 and U.S. Pat. No. 4,182,328. Other types of instruments can be used to dispense fluid like material into the uterine cavity and expand the balloon to move the material from the uterine cavity into the canals of the Fallopian tubes.

The reproductive system 20 has a uterus indicated generally at 22 joined to a pair of Fallopian tubes 23 and 24. The lower part of uterus 22 is joined to an enlongated vagina 26. Vagina 26 has a wall defining a vaginal passage 27 and an entrance or vestibule 28. The opposite end of vaginal passage 27 is in communication with a cervix 29. Cervix 29 is the lower part of the uterus extending from the isthmus of the uterus into the vagina. It is divided into supravaginal and vaginal parts by its passage through the vaginal wall. Cervix 29 has a normally closed exit opening or mouth 30 providing a passage from vaginal passage 27 to uterine cavity 31. Fallopian tubes 23 and 24, normally located opposite cervix 29, have passages or canals 32 and 33 which exit at mouths 34 and 35, respectively, into the top portions of urterine cavity 31.

Uterus 22 is a generally pear-shaped, thick-walled, hollow muscular organ. It consists of a main portion or body 37 terminating at the lower end in cervix 29. The upper part of uterus 22 has a top wall or fundus 36. The uteri of females vary in size, shape, wall thickness, wall strength, and sensitivity to pain. Also, the size and configuration of the uterine cavity 31 varies. Uterine cavity 31 is generally flat and rectangular in shape. Other sizes and shapes of uterine cavities have been noted. The exit section or mouths of canals 32 and 33 open to the top of uterine cavity 31 may be enlarged and elongated and are, in effect, extensions of the uterine cavity. The mid-portion of fundus 36 may extend down into the uterine cavity. The muscles of the cervix 29 vary in strength and size. In some instances, the cervical muscles are weak, providing minimal resistance to enlargement of cervical opening 30.

The dispensing instrument used with probe 21 includes an expandable balloon or sleeve 38 surrounding a chamber 39 for accommodating a fluid, such as air. The dispensing instrument is operable to expand the balloon 38 after it is inserted into uterine cavity 31. The material is dispensed into the uterine cavity 31 through the upper end of probe 21 after the balloon is partly expanded. Balloon 38 is then further expanded to move the material into canals 32 and 33 of the Fallopian tubes. The pressure of the fluid in chamber 39 is elevated to a predetermined limit to insure the expansion of balloon 38 to displace the uterine cavity. When the cervical muscles of cervix 29 are weak, balloon 38 can expand downwardly into vaginal cavity 27, as shown by balloon portion 38A. Balloon portion 38A will continue to expand, since it does not have to expand against the force of the uterine wall. This reduces the amount of the expansion of balloon 38 in the uterine cavity 31 so that the full displacement of the uterine cavity is not insured. The top of balloon 38 in FIG. 1 is shown spaced from fundus 36 and does not displace the entire uterine cavity 31. The instrument of the invention is provided with balloon support structure that fortifies and reinforces the balloon wall to prevent it from expanding through cervical opening 30 into vaginal passage 27.

Figure 3:
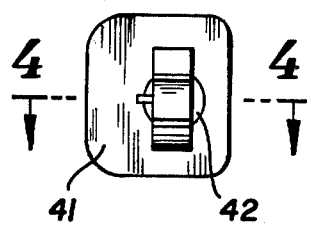
FIG. 3 is an end elevational view of the outside or lower end of FIG. 2.
Figures 2, 4:
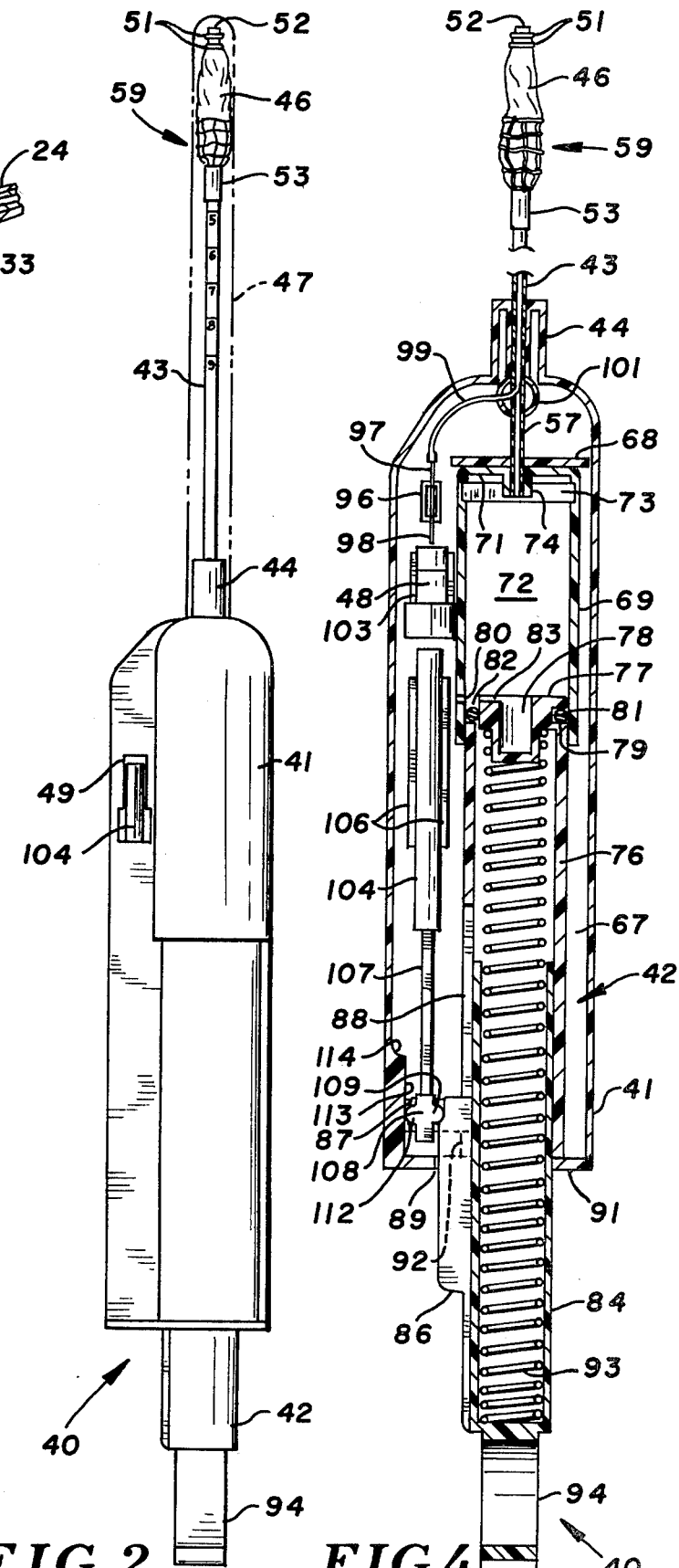
FIG. 2 is a top plan view of the material dispensing instrument of the invention.
FIG. 4 is a sectional view taken along line 4—4 of FIG. 3.

Referring to FIGS. 2, 3, and 4, the material dispensing instrument of the invention indicated generally at 40 is operable to transfer fluid like materials, as drug materials, into both canals of the Fallopian tubes of a reproductive system of a female. Instrument 40 has a housing or casing 41 accommodating a piston and cylinder assembly 42 and material dispensing structure hereinafter described. An elongated flexible tubular probe 43 is secured to and extends from the forward end 44 of housing 41. Probe 43 is located along the longitudinal axis of the housing and carries an expandable balloon or cylindrical sleeve 46. Balloon 46 is an expandable elastic tubular sheet member attached at its opposite ends to the outer or free end of probe 43. Balloon 46 is made of flexible, thin, air impervious sheet plastic material that is readily expanded or enlarged into a shape that coincides with the shape of the uterine cavity. Balloon 46 enlarges against the muscular wall of the body of uterus 22 to block the cervical opening 30. The muscular wall of the uterus provides a reaction force that permits the balloon 46 to enlarge and displace the uterine cavity. Balloon 46 is normally in the contracted position, as shown in FIG. 2. An elongated cylindrical cover 47, as shown in broken lines, is located over balloon 46 and probe 43 to protect and maintain the sterile condition of the balloon and probe. The open end of cover 47 is mounted on the annular end 44 of housing 41.

Figure 5:
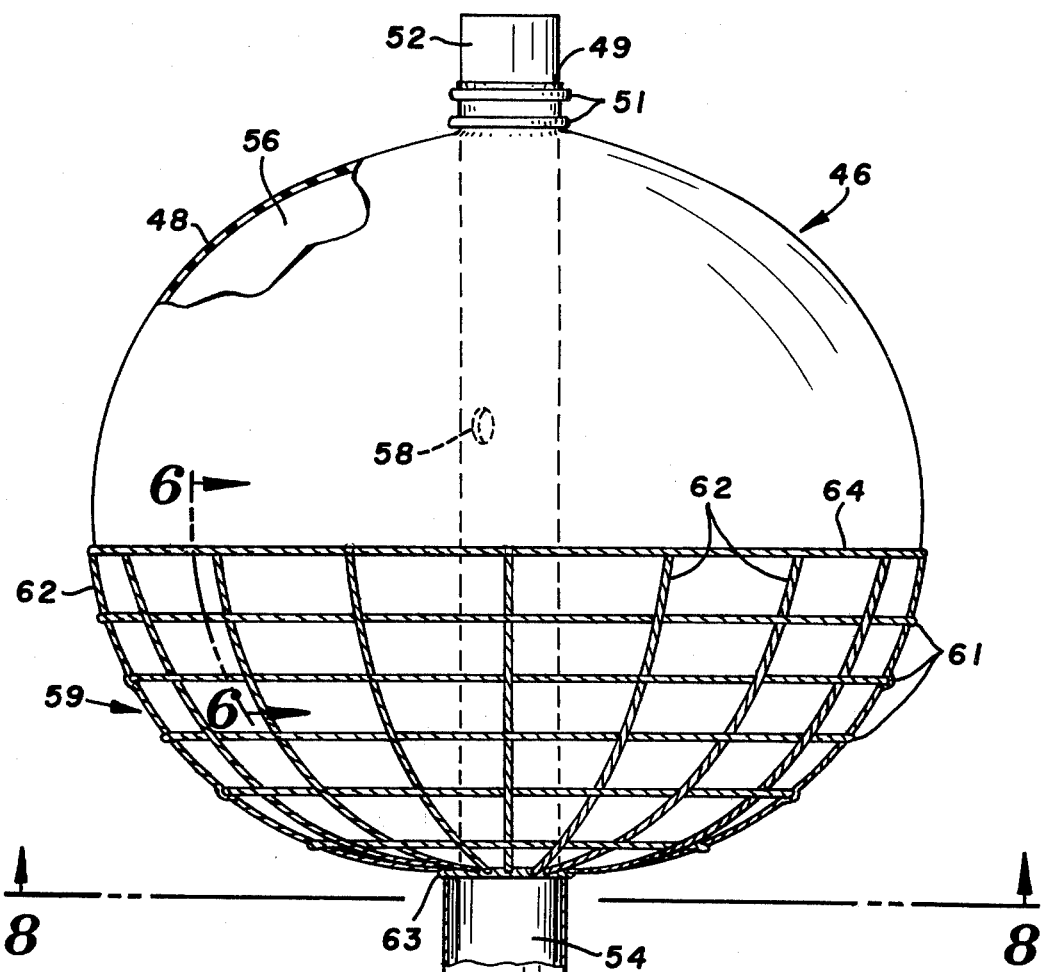
FIG. 5 is an enlarged plan view of the expanded balloon on the probe of the dispensing instrument.

Referring to FIG. 5, there is shown an enlarged expanded balloon 46 mounted on the remote end of probe 43. Balloon 46 has a cylindrical sheet member 48 of pliable elastic plastic material. The plastic material is thin and air impervious and has a generally tubular or cylindrical shape. The upper or outer end of sheet member 48 is in tight sealing engagement with the remote end of probe 43. A cylindrical collar 51 clamps outer end 49 about probe 43. Collar 51 is located a short distance below discharge end 52 of probe 43.

A second cylindrical collar or sleeve 53 clamps the inner end 54 of sheet member 48 to the outside of probe 43. Sleeve 53 is spaced below collar 51 whereby probe 43 extends longitudinally through a chamber 56 surrounded by the sheet member 48. Chamber 56 is in fluid communication with a longitudinal passage 57 of probe 43 through one or more holes 58 in the wall of probe 43.

A lower portion of sheet member 48 cooperates with support structure indicated generally at 59 which functions to control the expansion or enlargement of a lower portion of the sheet member 48 beyond a predetermined size. Support structure 59 cooperates with less than half of sheet member 48 to limit the enlargement of the lower portion of sheet member 48 by fortifying and reinforcing it after it has enlarged to a predetermined size. As shown in FIG. 5, support structure 59 cooperates with just under one-half of the lower portion of sheet member 48. Preferably, about 40% of the sheet member is covered by support structure 59. This distance between the horizontal diameter or plane passing through sheet member 48 and the top of the support structure 59 can vary. Support structure 59 can be confined to less than one-quarter of the lower one-half of sheet member 48. Support structure 59 can cover more than one-half of sheet member 48. Sheet member 48 when expanded outside the uterus has a generally globular like shape. Globular sheet member 48 can be viewed as two generally elongated semi-spherical sections comprising a first or lower section adapted to expand from adjacent cervical opening 30 up into uterine cavity 31. The second section is joined to the first section and closes the top of balloon 46. The upper end of the second section is attached with collar 52 to the remote end of probe 43. Support structure 59 cooperates with the first section to limit its expanded or enlarged size and reinforce the first section so that portions of the first section do not expand through cervical opening 30 and move out into vaginal passage 27. Support structure 59 is shown as a fabric like unit having latitudinal and longitudinal arranged fibers or filaments extended around the first section. The filaments are secured by suitable bonding or adhesive means to the outer surface of sheet member 48. The filaments extend from the lower end of the first section of sheet member 48 adjacent the collar 53 to a top filament which lies below the equator plane or largest diameter of balloon 46.

Figure 6:
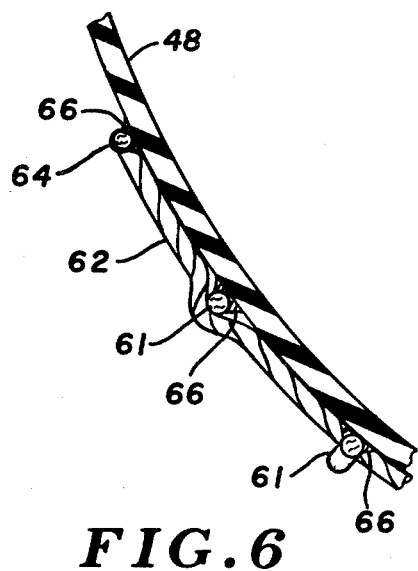
FIG. 6 is an enlarged sectional view taken along the line 6—6 of FIG. 5.

Support structure 59 is shown as having a plurality of circumferential circular endless filaments or lines 61. Filaments 61 are endless flexible circular members that are laterally spaced from each other and extend between a circular base filament 63 and a large diameter top or outside filament 64. Filaments 61 have different circular diameters and extend circumferentially around sheet member 48. Filaments 61, 63, and 64 are arranged in different latitudinal positions. Support structure 59, being made of flexible filaments, does not interfere with the initial expansion or enlargement of sheet member 48 in uterine cavity 31. Associated with filaments 61, 63, and 64 are a plurality of radially extended flexible filaments 62. Filaments 62 may be joined to and interweaved with filaments 61 to form a mesh or net. All the filaments can be knitted to form a cylindrical knitted net. Circumferential and radial filaments 61 and 62 are located in latitude and longitude arrangement on slightly less than the lower one-half of the generally hemispherical-shaped or globular like sheet member 48, as shown in FIGS. 5 and 6. Filments 61–64 are flexible to allow sheet member 48 to be collapsed onto probe 43 so that sheet member 48 and support structure 59 provide a minimum of resistance to the insertion of balloon 46 through cervical opening 30.

Referring to FIG. 6, filaments 61–64 are attached to the outside of sheet member 48 with an adhesive or bonding material 66. Suitable bonding materials, including adhesives and plastics, can be used to attach the filaments 61–64 to the sheet member 48. Other means and materials can be used to attach filaments 61-64 to sheet member 48.

Figure 7:
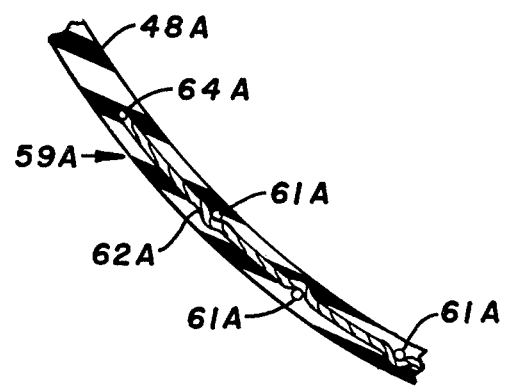
FIG. 7 is a sectional view similar to FIG. 6 showing a modification of the support structure of the balloon wall.
Figure 8:
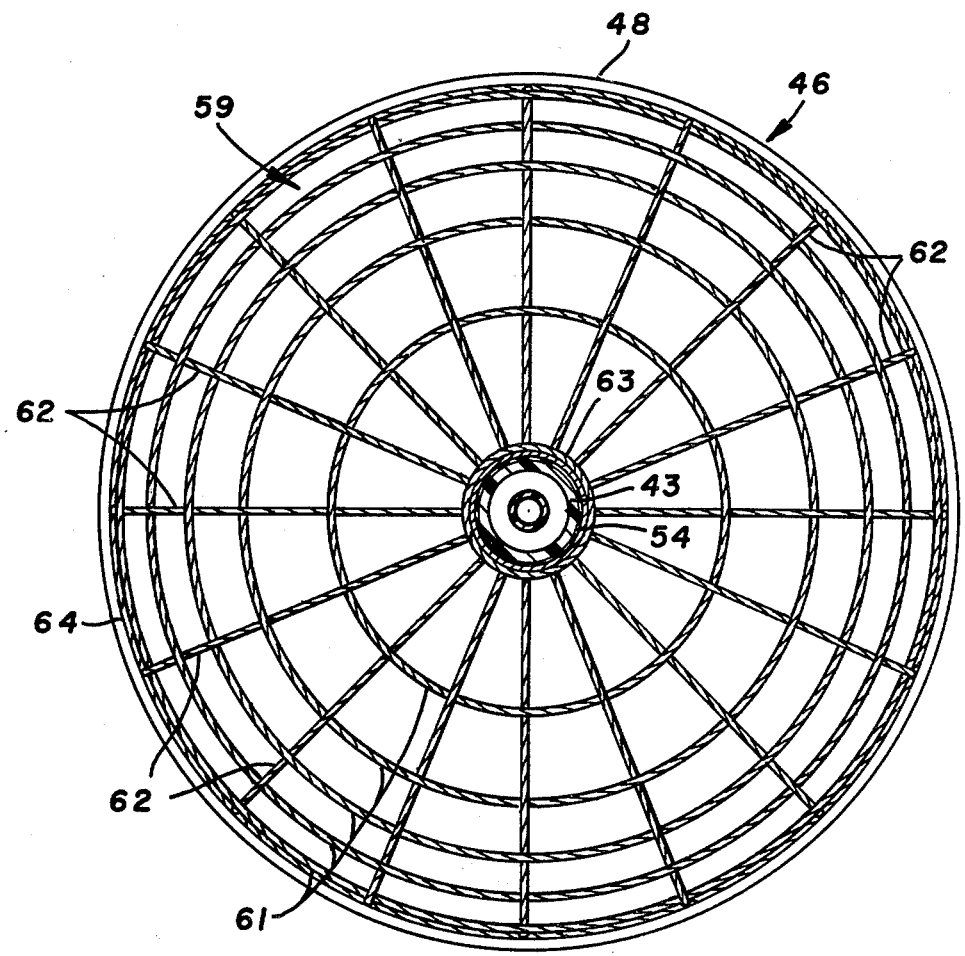
FIG. 8 is a sectional view taken along the line 8—8 of FIG. 5.
Figure 9:
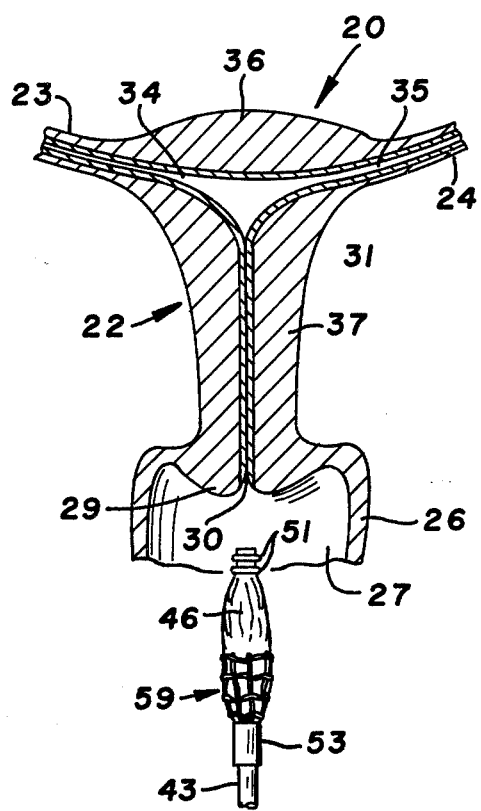
FIG. 9 is a sectional view of a female reproductive system prior to the insertion of the balloon and probe into the uterine cavity.

Referring to FIG. 7, there is shown a portion of a plastic sheet member indicated generally at 48A associated with support structure indicated generally at 59A. Support structure 59A includes a plurality of circumferential filaments 61A and 64A cooperating with radial filaments 62A. Filaments 61A-64A are embedded or contained within the plastic material of the sheet member 48. The parts of the sheet member, as shown in FIG. 8, correspond to the sheet member and support structure of FIG. 6 and have the same reference numerals with the suffix A.

In one form, support structure 59 is a nylon mesh net bonded to the outside of sheet member 48. The net extends from collar 53 to slightly below the mid-section of the sheet member 48. The nylon mesh is a seven (7) denier monofilament nylon. The nylon can be DuPont type 280 semi-dull. Other types of monofilament members can be used to form support structure 59.

Returning to FIG. 4, dispensing instrument 40 has an elongated hollow housing 41 having an inside chamber or cavity 67 accommodating piston and cylinder and assembly 42. The forward end of assembly 42 bears against a fixed transverse wall 68 secured to the forward end of housing 41. Assembly 42 includes a cylinder 69 having a closed forward end or bottom wall 71 surrounding a cylindrical chamber 72. The inside wall of cylinder 69 adjacent wall 71 has an annular pressure release groove 73. A short cylindrical boss 74 extends inwardly from the center of wall 71. The inner end of probe 43 is mounted in boss 74 and provides an air passage 57 from cylinder chamber 72 to chamber 56 surrounded by the sheet material 48 of balloon 46. The air in passage 57 flows through the holes 58 in probe 43 into the balloon chamber 56.

Assembly 22 also includes a movable piston 76 slidably located in cylinder 69. Piston 76 has a closed forward end or head 77. Head 77 has a forwardly open bore or recess 78 for accommodating boss 74 when piston 76 is in the full in position. Head 77 also has an annular outwardly open groove 79 accommodating a sealing or O-ring seal 81. The face of head 77 has a recess or cut-out segment 82 open to groove 79 and a short radial vent passage 83 connecting recess 78 to annular groove 79. Cut-out segment 82 and passage 83 provide an air passage between recess 78 and seal groove 79.

An actuator 84 having an elongated cylindrical tubular body is slidably located within piston 76. An elongated longitudinal rib 86 extends outwardly from one side of actuator 84. The forward end of rib 86 is connected to a pair of outwardly directed ears 87. The ears extend through a longitudinal slot 88 in the side of piston 76. Actuator 84 and rib 86 extend through an opening or hole 89 in the rear end wall 91 of housing 41. In use, actuator 84 is movable into housing 41 to locate piston 76 to a first full in position close to the bottom of cylinder 69. Piston 76 has inwardly directed lips 92 located adjacent opposite sides of rib 86 and engageable with the inside of end wall 89. Ribs 86 are engaged by ears 87 to limit outward movement of actuator 84 relative to piston 76. A coil spring 95 located longitudinally within piston 76 and actuator 84 biases the piston 76 and actuator 84 in opposite longitudinal directions. Lips 92 function as stops to hold piston 76 and actuator 84 in their relative extended positions.

A finger ring 94 is integral with the rear or outer end of actuator 84. Ring 94 is used by the hand of the operator to move actuator 84 into and out of housing 42 during the dispensing procedure.

Figure 10:
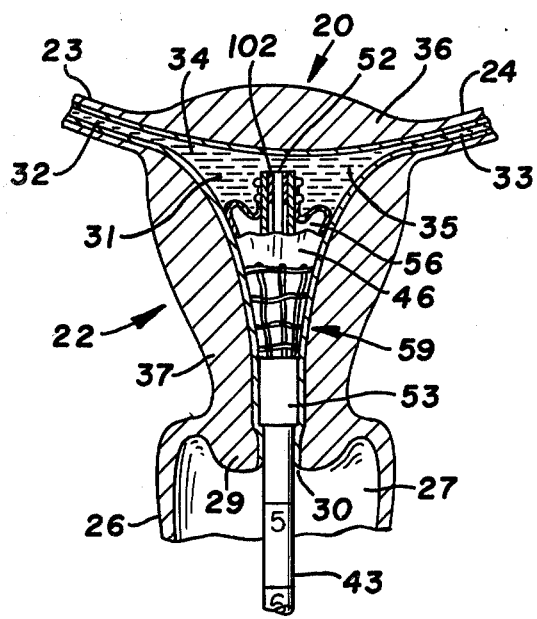
FIG. 10 is a view similar to FIG. 9 with the probe inserted into the uterine cavity and the balloon partially expanded.
Figure 11:
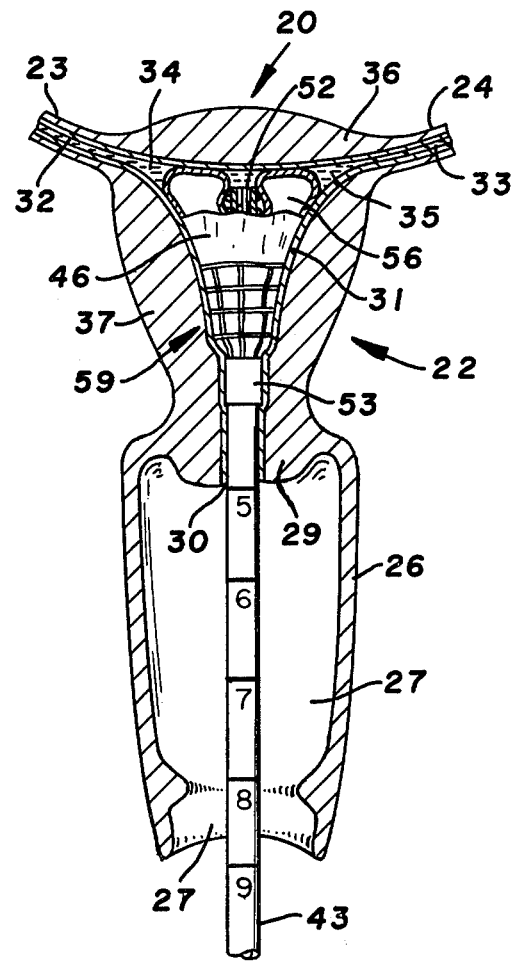
FIG. 11 is a view similar to FIG. 6 with the balloon fully expanded.

A support 96 located adjacent transverse wall 68 carries a longitudinal tubular needle 97. The forward or inlet end 98 of needle 97 projects in a rearward direction and faces the ampulla 48. The opposite end of needle 97 is connected to a tube or hose 99. Hose 99 extends through a hole in a post or support 101 attached to the forward end of housing 41. Post 101 also has longitudinal aligned holes accommodating and mounting the probe 43. Tube 99 extends into passage 57. As shown in FIG. 10, the upper or outer end of tube 99 is inserted into a plug 102. Plug 102 is mounted in the outer end of probe 43 in a manner to close the passage 57 of the probe 43. Tube 99 is free to discharge material into the uterine cavity 31 above balloon 46.

Returning to FIG. 4, housing 41 is provided with a cradle or holder 103 for accommodating ampulla 48. Cradle 103 positions ampulla 48 immediately in front of the sharp end 98 of needle 97. A longitudinal push rod 104 located adjacent ampulla 48 is operable to push ampulla 48 into needle 97 and force the material in ampulla 48 through the needle 97 and hose 99. Push rod 104 is slidably located between a pair of longitudinal ribs 106 secured to housing 42. The one forward or rear end or push rod 104 is integral with an elongated longitudinal neck 107 carrying a head 108. Head 108 has a first ear 109 located in a notch 111 in the forward portion of rib 86. Opposite first ear 109 is a second ear 112 riding on a linear edge 113 joined to a shoulder 114. The shoulder 114 accommodates the second ear 112 after the plunger has been initially moved on inward movement of the actuator 84. This structure is defined in applicant's U.S. Pat. No. 4,109,654 and is incorporated herein by reference.

In use, referring to FIG. 2, instrument 40 is packaged for shipment with cover 47 located over probe 43 and the balloon 46. The patient is prepared for treatment by the attending personnel in the operating theater. Cover 47 is removed by the physician to expose probe 43 and balloon 46. Push rod 104 is located in front of the opening 49 to prevent the accidental insertion of the ampulla into the instrument. The air that may be trapped in balloon 46 is evacuated or vented from balloon chamber 56 by pushing actuator 84 into housing 41. When actuator 84 is in its full in or first position, piston 76 is bottomed on or in engagement with wall 71. This locates O-ring seal 81 in alignment with groove 73 and the inside of cylinder 69 out of sealing engagement with the inside wall of cylinder 69. Air in balloon chamber 56, as well as passage 57 of probe 43, flows through recess 78 to vent passage 82 past the O-ring seal 81 and piston 76 to atmosphere. Actuator 84 is then retracted from housing 41 to move piston 76 away from wall 71. This establishes a vacuum force on the balloon 46 collapsing it into tight engagement with the end of probe 43. The vacuum force is established because O-ring seal 81 moves out of groove 73 into sealing engagement with the inside wall of cylinder 69. The instrument is now ready for insertion of the balloon 46 through the cervical opening 30 and into the uterine cavity 31. Support structure 49 associated with sheet member 48 of the balloon 46 does not interfere with the collapsing of the balloon 46 about the outer end of probe 43. The filaments are thin and flexible so as to permit sheet member 48 to collapse in tight engagement around probe 43.

Referring to FIG. 10, balloon 46 has been inserted through cervical opening 30 and is located in uterine cavity 31. Support structure 59, being attached to a portion of the sheet member 48, does not interfere with the insertion of balloon 46 through cervical opening 30. Balloon 46 and probe 43 can be rotated about the longitudinal axis of the probe during the insertion procedure to facilitate the slipping of balloon 46 through the cervical opening 30. The entire instrument can be rotated or twisted in opposite directions. Once balloon 46 is in the uterine cavity, actuator 84 is moved back to its full out or second position. Piston 76 is also moved to the outer end of cylinder 69 locating O-ring seal 81 outwardly of a small vent hole 80. With piston 76 exposing vent hole 80, air flows into cylinder chamber 72.

Push rod 104 is also moved to a rearward position by the ears 87 which engage head 108. Head 108 is moved on housing edge 113 and into notch 111 of rib 86. This locates push rod 104 out of alignment with the opening 49 so that ampulla 48 can be loaded into the instrument 20.

Ampulla 48, containing the drug material, is now located in cradle 103. The enlarged flange or head of the ampulla insures that the ampulla is properly positioned in the instrument. The detailed structure of ampulla 48 is disclosed and shown in FIGS. 12 and 13 of U.S. Pat. No. 4,182,328. The disclosure of this patent is incorporated herein by reference. Cradle 103 longitudinally aligns the pierceable end of the ampulla in alignment with needle 63. The open end of the ampulla containing the movable piston (not shown) is aligned with push rod 104.

Referring to FIG. 10, actuator 84 has been partially moved into housing 41. This movement moves piston 76 into the cylinder 69 and partially expands balloon 46. The support structure 59 does not interfere with the initial expansion of balloon 46, as the structure is flexible and not fully enlarged to its predetermined dimensions. Continued movement of actuator 84 moves push rod 104 into the ampulla 48 thereby forcing a drug material through needle 97, tube 99, and into the upper portion of uterine cavity 31. The drive connection between head 108 and rib 86 is maintained by notch 111 and linear edge 113. As soon as head 108 reaches shoulder 114 it is forced downwardly out of notch 111 thereby terminating the longitudinal movement of push rod 104. Actuator 84 is free to continue to be moved in an inward direction to fully expand balloon 46 to pump or move the drug material that has been discharged into the upper part of the uterine cavity into both canals 32 and 33 of the Fallopian tubes. The enlargement of balloon 46 displaces the volume of uterine cavity 31 to force the drug materials dispensed in the uterine cavity through the mouth areas 34 and 35 of the canals and into the canals 32 and 33 of the Fallopian tubes. Support structure 59 on balloon 46 is located in the lower or base portion of uterine cavity 31. Support structure 59 is forced into engagement with the inside wall of the uterus body 37. Support structure 59 allows only a predetermined controlled or limited expansion of the lower portion of the balloon 46. This prevents balloon 46 from expanding rearwardly or back through cervical opening 30 into the vaginal passage 27. Support structure 59 does not interfere with the expansion or enlargement of the upper portion of balloon 46 located in the central and upper portions of uterine cavity 31. The upper portion of balloon 46 progressively expands or enlarges when subjected to the air under pressure to effect the displacement or movement of the drug materials from uterine cavity 31 into canals 32 and 33 of the Fallopian tubes.

Balloon 46 is collapsed by withdrawing actuator 84 from the rear of housing 41. This moves piston 76 out of cylinder 69 thereby establishing a vacuum force in cylinder chamber 72. This quickly collapses balloon 46. Balloon 46 and probe 43 are then easily retracted from the uterine cavity through the cervical opening 30 and from the patient. Support structure 59 does not interfere with the collapsing of balloon 46, nor the withdrawal of balloon 46 from the patient.

The drug material moved into the canals of the Fallopian tubes by instrument 40 can be the drug materials identified in Bolduc U.S. Pat. No. 3,948,259. The drug materials identified in this Patent are incorporated herein by reference. These materials include a tissue adhesive, contraceptive drugs, biologicals, diagnostic materials, anaesthetic materials, as well as drugs and materials which enhance the fertilization and conception of a female.

While there has been shown and described a preferred embodiment of the dispensing instrument having an expandable balloon with support structure, it is understood that changes in the structure and materials can be made by those skilled in the art without departing from the invention. The invention is defined in the following claims.

The embodiments of the invention in which an exclusive property or privilege is claimed are defined as follows:

1. An instrument for placing material into both canals of the Fallopian tubes of a female having a uterus with a uterine cavity in communication with the canals of the Fallopian tubes, said uterus having a cervical opening in communication with the uterine cavity comprising: expandable means positionable in the uterine cavity adapted to be enlarged to substantially fill the uterine cavity, dispensing means supporting the expandable means and operable to dispense material into the uterine cavity in an area of the uterine cavity between the expandable means and the canals of the Fallopian tubes whereby said expandable means during the enlargement thereof moves the material from the uterine cavity into the canals of the Fallopian tubes, and means cooperating with said expandable means to support at least a part of said expandable means to prevent the expandable means from moving through the cervical opening leading to the uterine cavity during the enlargement of the expandable means.

2. The instrument of claim 1 wherein: said expandable means comprises an expandable balloon having a flexible wall, said means cooperating with said expandable means including means associated with part of said flexible wall to limit expansion of said part of said wall to prevent said part of said wall from moving through the cervical opening leading to the uterine cavity.

3. The instrument of claim 2 wherein: said means cooperating with said expandable means includes a fabric structure, and means for securing the fabric structure to said part of said flexible wall.

4. The instrument of claim 3 wherein: said fabric structure comprises a network of elongated flexible filaments, said filaments being secured to the part of said flexible wall by the means for securing the fabric structure to said part of said flexible wall.

5. The instrument of claim 3 wherein: said fabric structure comprises a monofilament nylon mesh net.

6. The instrument of claim 1 wherein: said expandable means has a flexible wall adapted to enlarge to substantially fill the uterine cavity, said wall having a first section located adjacent to the cervical opening when the expandable means is located in the uterine cavity and a second section expandable toward the mouths of the canals of the Fallopian tubes, said means cooperating with said expandable means to support at least a part of said expandable means comprising flexible filament means associated with said first section of the wall, and means to secure the filament means to said first section of the wall.

7. The instrument of claim 6 wherein: the filament means comprise monofilament nylon.

8. The instrument of claim 6 wherein: the filament means comprise a nylon mesh net.

9. The instrument of claim 6 wherein: said flexible wall when enlarged is a globular like body coinciding with the shape of the uterine cavity, said body having a first section located adjacent the cervical opening and extended into the uterine cavity and second section movable toward the mouths of the canals of the Fallopian tubes, said flexible filament means cooperating with at least a part of the first section to reinforce said part of the first section to prevent said part of the first section from moving through the cervical opening.

10. The instrument of claim 9 wherein: said flexible filament means cooperates with less than one-half of the body.

11. The instrument of claim 9 wherein: the filament means comprise monofilament nylon.

12. The instrument of claim 9 wherein: the filament means comprise a nylon mesh net.

13. An instrument for placing material into both canals of the Fallopian tubes of a female having a uterus with a uterine cavity in communication with the canals of the Fallopian tubes, said uterus having a cervical opening in communication with the uterine cavity and a vaginal passage comprising: a housing, an elongated probe mounted on the housing and extended therefrom, said probe having an outer end remote from the housing, a balloon mounted on the outer end of the probe, said balloon having a flexible sheet member provided with an outer end and an inner end, said sheet member surrounding the probe and defining a chamber adapted to accommodate air under pressure to enlarge the balloon into a globular like body coinciding to the shape of the uterine cavity, means mounting the outer and inner ends of the sheet member on the probe, said sheet member having a section extended from the inner end thereof toward the outer end thereof, support means cooperating with said section of the sheet member to limit enlargement of the section of the sheet member beyond a predetermined size thereby preventing the section of the sheet member from expanding through the cervical opening and into the vaginal passage, and means mounted on the housing for supplying air under pressure to the chamber to enlarge the balloon and to dispose material into the uterine cavity between the balloon and canals of the Fallopian tubes, said balloon being enlarged to a size to move the material from the uterine cavity into the canals of the Fallopian tubes.

14. The instrument of claim 13 wherein: said support means including a fabric structure surrounding the section of the sheet member, and means for securing the fabric structure to said section of the sheet member.

15. The instrument of claim 14 wherein: said fabric structure comprises a network of elongated flexible filaments.

16. The instrument of claim 15 wherein: said flexible filaments are arranged in intersecting latitudinal and longitudinal directions on said section of the sheet member.

17. The instrument of claim 16 wherein: each of said fabric filaments is a monofilament structure.

18. The instrument of claim 13 wherein: said section of the sheet member and support means cooperating with the section of the sheet member comprise less than one-half of the longitudinal length of the sheet member.

19. The instrument of claim 13 wherein: the support means include elastic filament means, and means attaching the filament means to said section of the sheet member.

20. The instrument of claim 13 wherein: said support means includes elongated flexible filament means embedded in the material of the section of the sheet member.

21. A balloon for use with an instrument for placing material into both canals of the Fallopian tubes of a female having a uterus with a uterine cavity in communication with the canals of the Fallopian tubes, said uterus having a cervical opening in communication with the uterine cavity and the vaginal passage, said instrument having dispensing means operable to dispense material into the uterine cavity comprising: a flexible sheet member mounted on a portion of the dispensing means defining a chamber adapted to accommodate air under pressure to enlarge the sheet member into a globular like body coinciding to the shape of the uterine cavity when said balloon is located in the uterine cavity, said sheet member having a first section locatable adjacent the cervical opening and extended into the uterine cavity and a second section adapted to be enlarged toward the canals of the Fallopian tubes and support means cooperating with the first section of the sheet member to limit enlargement of the first section beyond a predetermined size thereby preventing the first section of the sheet member from expanding through cervical opening into the vaginal passage.

22. The balloon of claim 21 wherein: said first section of the sheet member is smaller than the second section of the sheet member.

23. The balloon of claim 21 wherein: said support means includes fabric structure, and means for securing the fabric structure to said first section.

24. The balloon of claim 23 wherein: said fabric structure comprises a network of elongated flexible filaments.

25. The balloon of claim 23 wherein: said flexible filaments comprise monofilament nylon.

26. The balloon of claim 23 wherein: said flexible filaments are arranged in intersecting latitudinal and longitudinal directions around said first section of the sheet member.

27. The balloon of claim 21 wherein: said support means includes flexible filaments arranged about the first section, and means to attach the filaments to said first section of the sheet member.

28. The balloon of claim 27 wherein: each filament has a monofilament structure.

* * * * *

UNITED STATES PATENT AND TRADEMARK OFFICE
CERTIFICATE OF CORRECTION

PATENT NO. : 4,207,891
DATED : June 17, 1980
INVENTOR(S) : Lee R. Bolduc

It is certified that error appears in the above-identified patent and that said Letters Patent are hereby corrected as shown below:

Column 5, line 23, delete "and" after "cylinder".

Signed and Sealed this

Second Day of September 1980

[SEAL]

Attest:

SIDNEY A. DIAMOND

Attesting Officer

Commissioner of Patents and Trademarks